United States Patent [19]
Podnar et al.

[11] Patent Number: 6,108,634
[45] Date of Patent: Aug. 22, 2000

[54] COMPUTERIZED OPTOMETER AND MEDICAL OFFICE MANAGEMENT SYSTEM

[76] Inventors: Paul J. Podnar, 18916 Arrowhead, Cleveland, Ohio 44119; Gregg W. Podnar, 1046 S. Trenton Ave., Pittsburgh, Pa. 15221

[21] Appl. No.: 08/631,562

[22] Filed: Apr. 12, 1996

[51] Int. Cl.[7] ................................................ A61B 3/18
[52] U.S. Cl. .................................... 705/2; 351/200
[58] Field of Search ............................ 364/525, 550; 351/200, 201, 223, 239, 243, 246; 348/55, 59, 51, 52, 42; 705/1, 2, 3

[56] References Cited

U.S. PATENT DOCUMENTS

| | | | |
|---|---|---|---|
| 4,567,513 | 1/1986 | Imsand | 348/55 |
| 4,987,487 | 1/1991 | Ichinose et al. | 348/59 |
| 5,026,151 | 6/1991 | Waltuck et al. | 351/246 |
| 5,035,500 | 7/1991 | Rorabaugh et al. | 351/226 |
| 5,206,671 | 4/1993 | Eydelman et al. | 351/203 |
| 5,357,277 | 10/1994 | Nakayoshi et al. | 348/55 |
| 5,550,602 | 8/1996 | Braeuning | 351/243 |
| 5,589,897 | 12/1996 | Sinclair et al. | 351/223 |
| 5,694,199 | 12/1997 | Rodriguez | 351/223 |
| 5,828,943 | 10/1998 | Brown | 434/258 |

*Primary Examiner*—Melanie A. Kemper
*Attorney, Agent, or Firm*—Arter & Hadden LLP

[57] ABSTRACT

A computer-based system supports testing and analysis of vision patients. The system employs a multi-media interface, high-resolution, flickerless color video displays for both a patient and a clinician. These displays work in concert with a computer-based system which includes software adapted to support a clinician testing a patient's visual capabilities. The system forms a component of a full medical office management facility which is extended to allow archiving of patient data, account information, office environment control, and patient education.

19 Claims, 6 Drawing Sheets

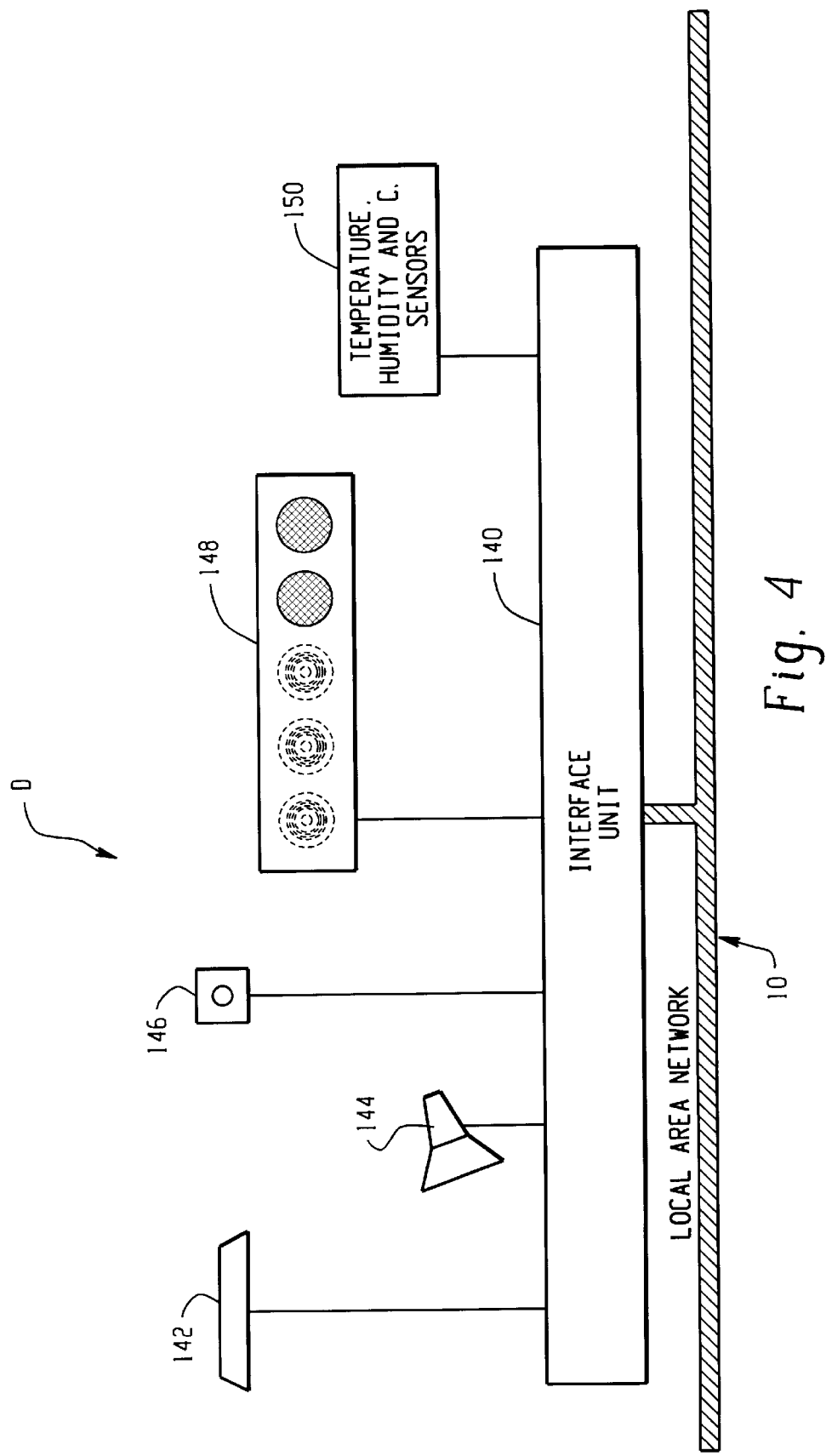

MATCH TO FIG.5B

COMPUTERIZED OPTOMETER AND MEDICAL OFFICE MANAGEMENT SYSTEM

BACKGROUND OF THE INVENTION

This application pertains to the art of medical office automation and more particularly to the automation of offices used by vision care professionals.

The invention is particularly applicable to the testing and analysis of vision patients and will be described with particular reference thereto. However, it will be appreciated that the invention has broader application such as in the automation of any clinical office environment to achieve enhanced diagnosis and treatment, streamlined patient turn-around time, and overall patient satisfaction.

There has been increasing reliance on automation in virtually every area of business. The medical profession is perhaps one of the slowest to embrace and adapt automation technology to its practices. This is particularly true in the clinical environment in which patients are seen and diagnosed and treatment is prescribed or administered.

Of course, an ideal clinical environment from a patient's perspective is first-class medical care, low costs, and a minimal inconvenience. These desires are also mirrored by the clinicians.

Today, clinical offices implement automation in such areas as word processing, database manipulation, accounts payable, and accounts receivable. While the benefit of automating these areas is accepted, they provide a piecemeal approach to achieving the above-described goals.

The present invention contemplates a new and improved clinic automation system which overcomes the above-referred problems, and others, and provides a complete medical office diagnosis and treatment system which enhances the quality of treatment and patient satisfaction. The system also provides for increased efficiency that will minimize inconvenience to the patients while allowing a clinician to diagnose and treat patients rapidly, thus lowering overall costs.

SUMMARY OF THE INVENTION

In accordance with the present invention, there are provided clinician and patient examination stations. The clinician station is provided with a high-resolution, flickerless, color video display having software-changeable, touch screen controls. Means is provided to allow a clinician to activate easily these various controls. Such means includes one or more of a pointing device, speech recognition device, a foot switch or switches, wireless keypad or keyboard. An audio output, such as a speaker system or head phones is also provided. A patient is provided with a corresponding patient station which also includes a high-resolution, flickerless, color video display. The patient's station is also suitably provided with one or more of input/output devices including loud speakers, headphones, speech or sound recognition, pointing device, keyboard, or the like. The patient station and the clinician station are placed in data communication with one another and operate under specified software to accomplish clinician-supervised, automated patient testing and analysis.

In accordance with another aspect of the present invention, a plurality of clinician/patient examining stations are networked so as to be in data communication with one another.

In accordance with yet another aspect of the present invention, clinician/patient examination stations are networked so as to be in data communication with one or more of office-assistant workstations, environment monitoring and control interfaces, telephony, and video, both for instruction and entertainment.

In accordance with yet another aspect of the present invention, a networked system as described above is provided with more traditional, office-automation capabilities such as printing equipment, telephone equipment, database equipment, and the like.

An advantage of the present invention is the provision of a clinical office automation system which provides streamlined patient throughput, more accurate testing, and more thorough data acquisition.

Yet another advantage of the present invention is the provision of a medical office automation system which lessens costs and enhances profitability by allowing a clinician to effectively service patients at a faster rate, thus lower overall costs.

Yet another advantage of the present invention is the provision of an office automation system which is readily adaptable to small children, multiple languages, and alternative analyses for patients suffering various physical impairments thereby facilitating the treatment of a greater variety of patients and ailments.

Further advantages will become apparent to one of ordinary skill in the art upon a reading and understanding of the subject specification.

SUMMARY OF THE DRAWINGS

The invention may take physical form in certain parts, and arrangements of parts, a preferred embodiment of which we described in detail in this specification and illustrated in the accompanying drawings which form a part hereof, and wherein:

FIG. 4 is a block diagram of an environmental interface unit another subsystem of an overall medical office control system, showing interconnections between an interface unit and input/output ("I/O") devices.

DETAILED DESCRIPTION OF THE PREFERRED EMBODIMENT

Figure 1:
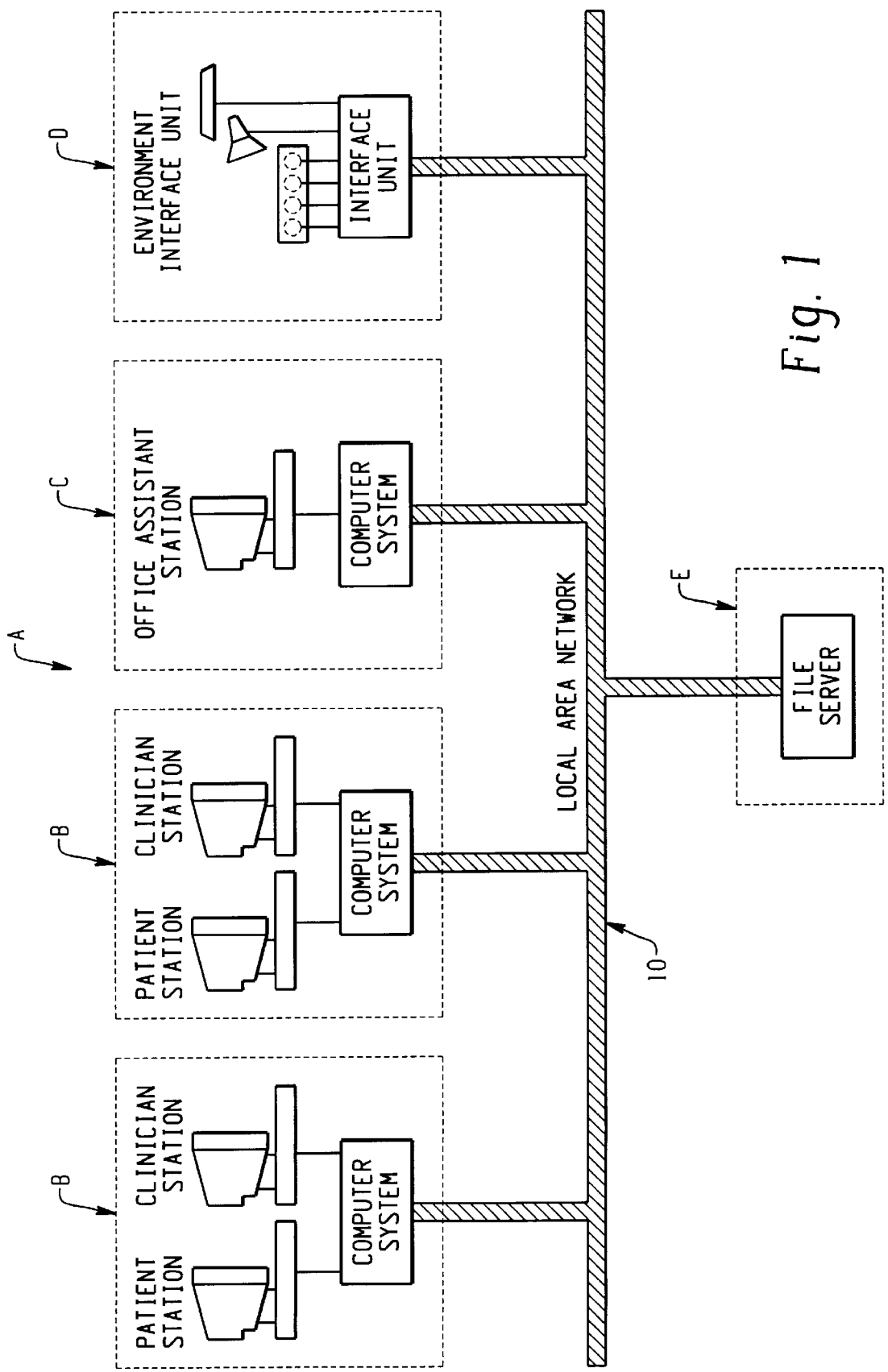
FIG. 1 is a diagram of a complete automated medical office system of the subject invention, along with various interconnected functional subsystems.

Turning now to the drawings wherein the showings are for the purpose of illustrating the preferred embodiment of the invention only, and not for the purpose of limiting the same, FIG. 1 showed an automated medical office system A which includes patient and clinician stations B, an office assistant station C, an environment interface unit D and a file server E. All stations/subsystems of the automatic medical office system A are interconnected via a local area network ("LAN") 10. The automated medical office system A is advantageously comprised of each of the sub-units B–E to allow for a completely integrated patient handling and office management system. However, various sub-combinations of the structure provide specific advantages to certain aspects of medical office use. It will be appreciated that the system is also advantageous to selective automation of various aspects of patient management and care. The system also contemplates for selective addition of functionality as needs or desires for automation mature.

Next, the patient/clinician stations B, which are further illustrated in FIG. 2, will be discussed in detail. The portion B advantageously includes a computer system 20 which is provided for data acquisition, processing and analysis, as well as communication with external or peripheral components. The computer system 20 also provides data translation with the LAN 10, the telephone modem 22, and the expansion capabilities 24. The computer system with the aforenoted functionality is readily fabricated from conventional computer components. The base computer system 20 includes a central processing unit ("CPU") 26, a random access memory ("RAM") 28, and bulk storage 30, such as magnetic and/or optical disk storage. The computer system 20 also includes one or more audio digitizers 32, and video digitizers 34 which provide multi-media capability the particulars of which are well within the understanding of one skilled in the art.

The computer system 20 advantageously features a patient video display unit ("VDU") 36. The clinician is also advantageously provided with an analogous video display unit VDU 38. It is contemplated that a wireless remote display unit that can be carried by a clinician may be exchanged for the clinician's VDU 38. The computer system 20 includes graphical display generators 40 and 42 which form a signal communication link with VDU 36 and VDU 38 respectively. The computer system 20 may include additional graphic display units beyond 40 and 42 to interface with additional VDU's.

In the preferred embodiment, VDU's 36 and 38 advantageously are high resolution, flickerless, color display units. The term "flickerless" refers to the refresh rate of a VDU. In particular, a "flickerless" VDU is one with a refresh rate sufficiently high such that individual refreshes cannot be perceived by the human eye, but appear fused into a continuous image on the video display unit. Flickerless monocular testing requires a refresh rate of approximately 60 Hertz or greater. This rate depends on the image presented, the room and screen luminance, the field of view and other factors which are well within the understanding of one skilled in the art.

When the system is used in conjunction with patient binocular vision testing, the refresh rate is advantageously set to allow for binocular vision. When used in conjunction with the binocular eyewear noted below, each eye is presented with a different image. Both the testing of depth perception by using stereoscopic image pairs, and the testing of each eye individually by presenting different images to each eye are well within the understanding of one skilled in the art. A binocular refresh rate is generally double the rate for flickerless, monocular testing. The preferred embodiment advantageously features a refresh rate of anywhere between 120 and 150 Hertz. However, the refresh rate may be higher than 150 Hertz to achieve the same result. The actual refresh rate employed by this disclosure within the range specified is highly application specific.

In the preferred embodiment, one or both of the patient VDU 36 and the clinician VDU 38 suitably incorporate a touch screen to allow for user interaction via a graphical user interface ("GUI"). The system advantageously employs highly configurable, structured GUI for both the clinician and patient. The particulars of the GUI of the subject invention will be detailed below. Such interface or other user interfaces identified below will advantageously allow patients to enter pre-examination information.

In addition to VDU's 36 and 38, a Patient and Clinician Station B features several other suitable devices that provide audio-video interaction capability. When the system is used in conjunction with vision patient services, such devices include binocular eyewear including the flickerless binocular eyewear 44 and the flickerless occlusion shutters 46. A binocular control signal is suitably provided from the computer system 20 to one or both of the flickerless binocular eyewear 44 and the flickerless occlusion shutters 46, through a binocular controller 48.

Further audio-visual interaction capability of Station B includes speakers, such as stereophonic speakers 50; headphones, such as stereophonic headphones 52; and a microphone, or other audio input device illustrated at 54. The computer system 20 provides for selected audio output capability through monophonic and/or stereophonic sound output through the connection 56. The computer system 20 is advantageously provided with audio digitizers 32 to communicate with devices such as the microphone 54 noted above.

Additionally, the hardware embodiment of the Station B is also advantageously provided with a video input. Such video input suitably includes one or more of a video disk player 60, video cassette player 62, a high resolution still video camera 64, a motion video camera 66 and binocular video camera 68. Each of these devices is also placed in signal communication with the computer system 20. The computer system 20 advantageously includes video digitizers 34 for communicating with one or more of the video disk player 60, video cassette player 62, still video camera 64, motion video camera 66 and binocular video camera 68.

Figure 2:
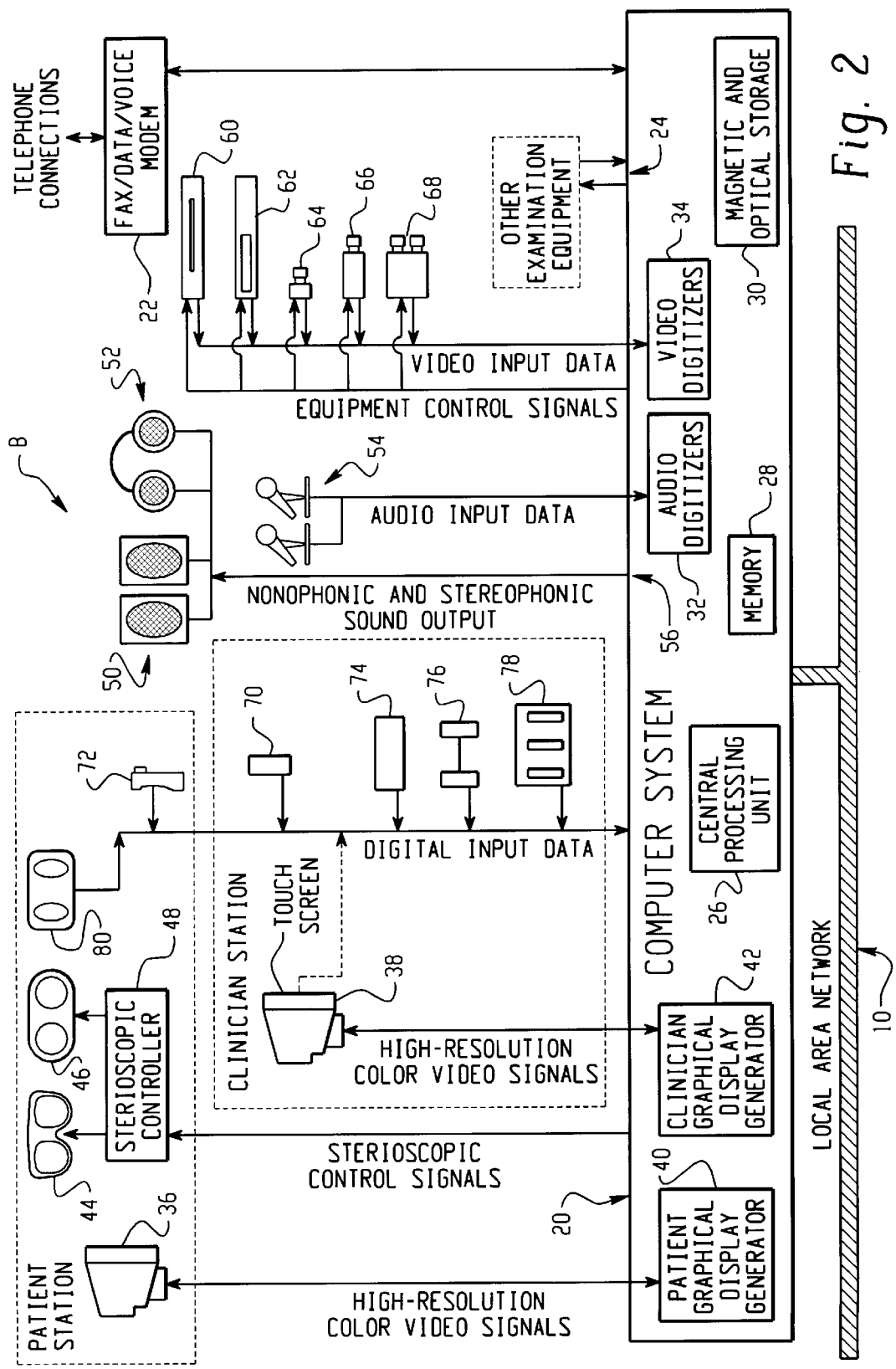
FIG. 2 is a block diagram of a patient and clinician station, a subsystem of an overall medical office control system, showing interconnections between a computer system and input/output ("I/O") devices.

As illustrated by FIG. 2, several other, input units are selectively incorporated into the patient/clinician unit B. Any such unit is placed in signal communication with the computer system 20. These include a mouse/pen/tablet (collectively or alternatively "pointing device") 70, response buttons 72, keyboard 74, wireless remote controls 76, foot switches 78 and eye closure sensors 80.

It will be appreciated that the system provides for upgradeability and expandability. The system is therefore advantageously provided with general expansion capabilities 24 to accommodate modifications, including but not limited to, the control of and data gathering from other examination equipment.

The patient/clinician station B is also advantageously provided with external communication ability. Such capability would allow immediate reception and analysis of remotely stored data such as patient medical history, records, diagnostic imagery and the like. This external communication capability also allows access to networked computer service providers and a variety of telephony applications such as voice communication, computer-based teleconferencing, data sharing through "white board" applications and the like. Such external communication capability is suitably provided by a telephone modem 22 which may include one or more of a fax, data or voice transmission capabilities. The computer system 20 also provides data translation between the expansion unit 24 and the external data communication unit 22.

In the preferred embodiment, the patient/clinician stations B are connected to a LAN 10 which allows access and modification of data stored in the other stations and communication of information among all the stations so connected. This includes but is not limited to patient records stored in the file servers E, monitoring of information shared among patient/clinician stations B and office assistant stations C. Such LAN's are readily available and may include such common network interconnections as ethernet, token-ring, and the like and employ communication protocols such as IPX/SPX, TCP/IP, etc. It will be appreciated that other units or stations may be connected to the LAN as they are added to the automated medical office system A.

Figure 3:
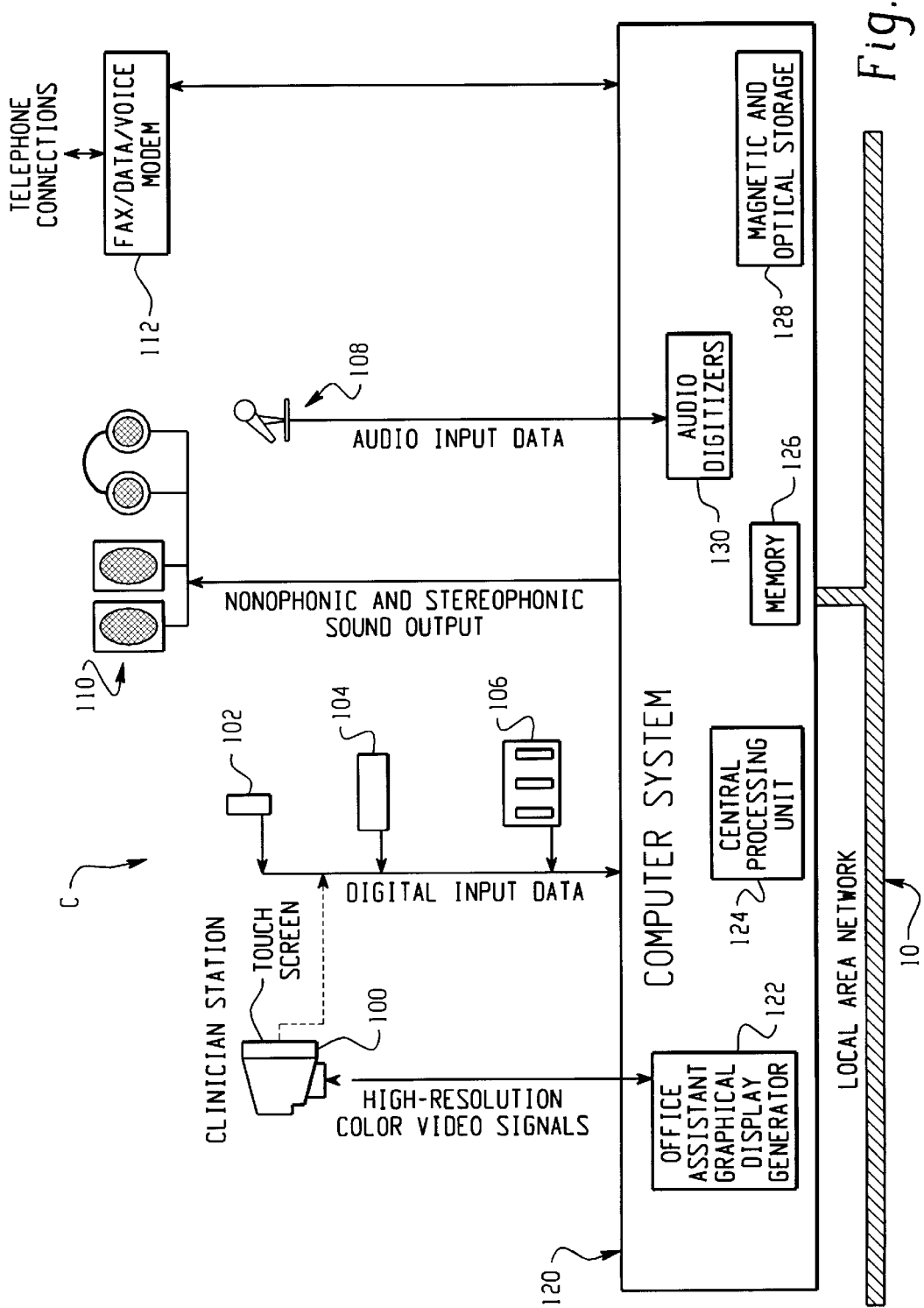
FIG. 3 is a block diagram of an office assistant station, another subsystem of an overall medical office control system, showing interconnections between a computer system and possible input/output ("I/O") devices.

Turning next to the office-assistant station C of FIG. 3, included is an office-assistant high-resolution, flickerless, color video display unit ("VDU") 100. This VDU is suitably similar to that of the VDU's 36 and 38. The station C is also, advantageously provided with one or more of a pointing device 102, keyboard 104, foot switches 106, audio input 108, audio output 110 and external data communication unit 112. These sub-systems are also advantageously provided in a format similar to that noted in connection with the patient/clinician stations B.

In the preferred embodiment, the office-assistant station provides for clerical, patient routing, transcription, word processing database-related support. Also, such station may also include various timekeeping functions to remind clinicians or others of various events such as, by way of example and not limitation, how long a patient has been waiting or other occurrences. Such timing functions may also advantageously display on any VDU that is part of the automated medical office system A. Thus, the system is also ideally provided with an independent computer system 120. However, it will be appreciated that the computer system 20 may also do these tasks.

The computer system 120 is provided in the preferred embodiment insofar as many of the functions associated with the office-assistant station C are processor intensive and/or data intensive. The computer sub-system 120 suitably includes its own graphical display generator 122, analogous to that 40 and 42 as described above. It also includes a CPU 124, RAM memory 126, bulk storage 128, and audio digitizer 130, each of which is analogous to that described above in connection with a computer system 20. In addition, interconnections for signal and signaling/data between the computer sub-system 120 and its various external components is also provided.

In the preferred embodiment, the office-assistant station C is connected to the patient and clinician stations B, the environmental interface unit D, and the file server E via a local area network ("LAN") 10. This interconnection provides for a well integrated system. Patient information is readily available to both the clinician, as well as the office-assistant. Thus, information is available for both diagnostics, invoicing, archiving and -the like. Clinician inputs, such as direct voice input, are also available to office-assistant station personnel. This allows for ease in transcription from dictation, record updating, and the like.

Turning now to FIG. 4, the subject automated medical office system A is also advantageously provided with one or more of the environmental interface unit D. This unit is also provided with an interconnection sub-system 140 which is tied into LAN 10 along with the patient and clinician stations B, the office-assistant station C, and the file server E. The environment interface units D suitably provide for the selective control of one or more room lights 142, task lights 144, fixation lights 146 and annunciator lights and signals 148. Further, the unit provides environmental monitoring for items such as temperature, humidity and the like, and is provided with a sensor unit 150. Thus, environmental, and related input such as dimming of lights, monitoring of temperature, external status such as room-in-use and help-needed are advantageously provided and fully integrated into the overall system. This is advantageous as such information can be included in patient records created during an examination. Such information may be useful in diagnosis of patients.

Figure 5A:
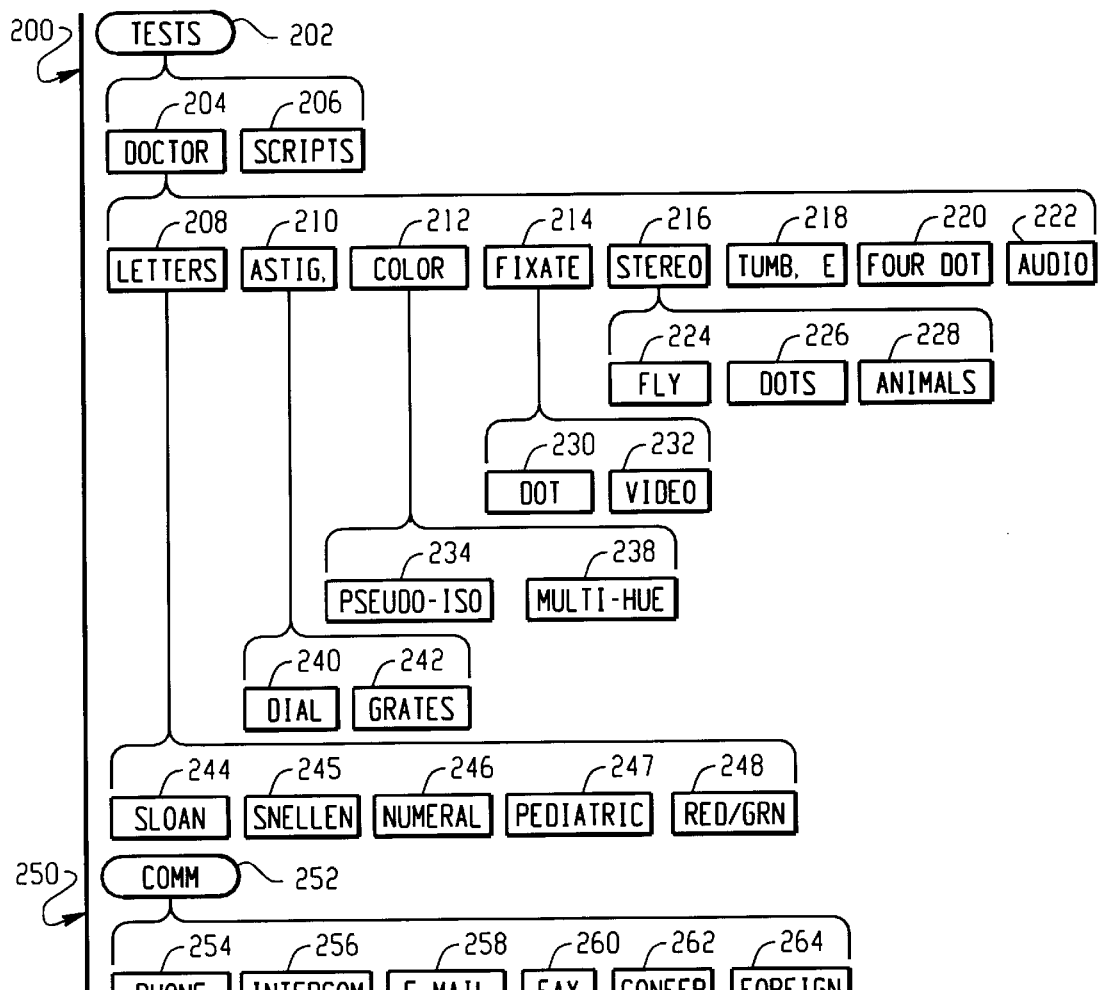
FIGS. 5A and 5B show a functional layout of a control screen hierarchy of the subject invention
Figure 5B:
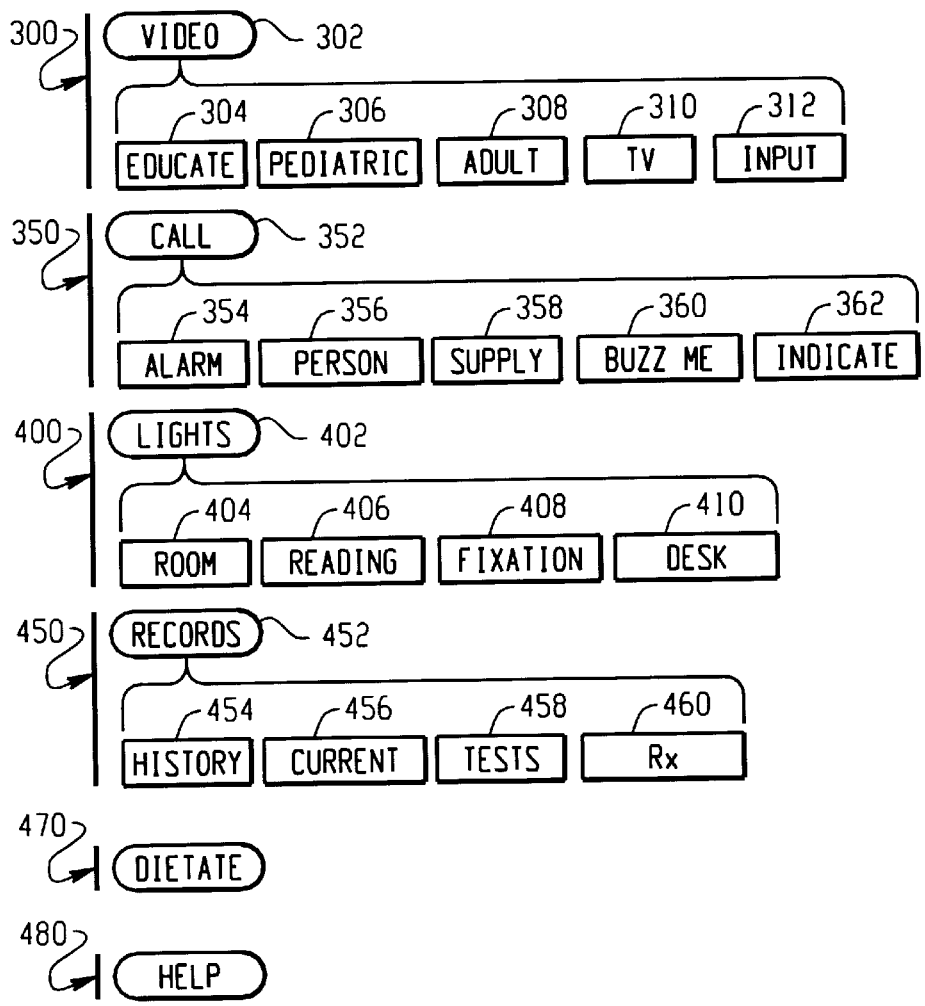

Turning now to FIGS. 5A and 5B, a hierarchical relationship of major screen functions of the associated invention will be described in detail. In the FIGURES, several sections are provided. These include a test section 200, a communication section 250, a video section 300, a call section 350, a light section 400, and a records section 450. Each such section represents a top-level control screen represented by the first rounded box of each section.

Turning particularly to the test section 200, the top level screen 202 defines the entry level of the section. This section allows for further selection of individual tests for predefined scripts of tests for individual patients or patient types. Such scripts advantageously include an initial set. The system also provides for custom groups which are definable by clinicians. The further selection of individual tests is selected by the "doctor" button 204. The scripts are selected by the scripts section 206.

The doctor selection 204 provides for tests associated therewith to be broken down by types and within each type thereof. In the illustration, the doctor selection allows for selection of letters at block 208, astigmatism at block 210, color at block 212, fixation at block 214, binocular testing at block 216, tumbling "E" at block 218, four dot at block 220, and audio at block 222.

In the illustration, it will be noted that the stereo block 216 calls, in turn, selectively to fly block 224, dots block 226, and animals block 228. Selections under the fixate menu 214 include a dot block 230 and a video block 232. Selections under the color menu 212 suitably include a pseudo-isochromatic test menu 234 and a multi-hue test menu 238. Suitable selections under the astigmatism menu 210 suitably include a dial selection 240 and a grates selection 242. Finally, under the tests menu 200, the letters selection 208 suitably leads to the selection of sloan 244, snellen 245, numeral 246, pediatric 247, and red/green 248 as test alternatives.

Turning next to communications section 250, provided is access to a wide range of communication tools. Working from top level menu 252, these suitably include a phone selection 254, intercom selection 256, e-mail selection 258, fax selection 260, conferencing selection 262, and foreign selection 264, such as a translation function.

Turning next to video block 300, opening screen 302 provides selections for education at block 304, pediatric at block 306, adult at block 308, television at block 310, and user input at block 312. Such video fixation allows for animations, "house" video, and educational explanations of dysfunctions and procedures. Video capture from input devices, such as microscopes and cameras, is also suitably accessible through this selection.

Turning next to the call 350, the top menu 352 suitably provides links to an alarm block 354, personnel block 356, supply block 358, "buzz me" block 360, and indicate block 362. In the preferred embodiment, both on-screen and annunciator lights/signals are controlled through the call selection 352.

Turning next to the lights section 400, opening or top menu 402 provides suitable selection of a room block 404, reading block 406, fixation 408, and desk block 410. The system provides for selected control of room lights and certain equipment such as fixation and glare lights and x-ray light box viewers, and the like.

Turning next to records section 450, the opening records menu 452 suitably provides selection to a history block 454, a current block 456, a test block 458, and a prescription block 460. Thus, the system provides for selected access to patient records, currently-recorded test results, previous results, and prescriptions. This suitably encompasses multimedia records, including digital photographs, video clips, audio dictation, charts, text, and the like. The dictate menu 470 provides for audio dictation by a clinician into a patient record. Each dictation is also suitably queued for later transcription by front-office staff. Further, both an audio record and a textual transcription are selectively kept in a permanent record associated with the particular patient.

Next, block 480 provides a help access menu. This provides access to appropriate help based commands which are based on the particular context from which the command was invoked. For example, the help will provide an explanation of an operation of certain tests which will be available quickly as each test is selected. Further, an explanation of system functions are also advantageously provided. In the preferred embodiment, full access to a complete help system is available at all points in the menuing hierarchy to the clinician.

The invention has been described with reference to the preferred embodiment. Obviously, modifications and alterations will occur to others upon a reading and understanding of this specification. It is intended to include all such modifications and alterations insofar as they come within the scope of the appended claims or the equivalents thereof.

Having thus described our invention, we now claim:

1. A computerized vision patient examination and medical office management system comprising:
    at least one examination station, each examination station including:
        (A) a processor system including,
            a central processor unit,
            random access memory disposed in the address space of the central processor unit for holding instructions and data,
            an input/output unit adapted to send and receive digital signals to and from the central processor unit,
            a display generator for selectively generating visual stimuli images based on preselected criteria, and
            a stereo signal controller selectively outputting a digital, binocular control signal;
        (B) a clinician unit in data communication with the processor system including,
            a first color video display unit adapted to display digital images based on preselected criteria, set by the processor system,
            a first data input unit adapted to receive practitioner input, and
            means for controlling the processor system in accordance with data received into the first data input unit;
        (C) a patient unit in data communication with the processor system including,
            a second color video display unit adapted to display digital images, including visual stimuli images, set by the processor system which is adapted to accommodate a scan rate of over 120 Hertz,
            a graphical generator for generating graphical images on the second color video display unit,
            a second data input unit adapted to receive patient data,
            means for communicating data representative of patient input to the processor system, and
            stereo signal output means adapted for selectively outputting the digital, binocular control signal received from the processor system to an associated binocular flickerless viewing system; and
        (D) an audio output unit adapted to output digital audio sounds set by the processor system.

2. The system of claim 1 further comprising an audio input unit adapted for selectively communicating digital audio signals, set by an associated audio receiver, to the processor system.

3. The system of claim 1 further comprising a controller interface adapted to selectively control room lighting in accordance with an output of the processor system.

4. The system of claim 3 further comprising a patient information database unit accessible by the at least one examination station.

5. The system of claim 4 wherein the patient information database includes means for storing digitized patient records inclusive of images and sounds.

6. The system of claim 5 wherein the second data input unit is comprised of a touch-screen interface integrated with at least one of the first and second video display units.

7. The system of claim 6 wherein the stereo signal controller includes means for selectively outputting the digital, binocular control signal to a flickerless binocular viewing system.

8. A method of computer-assisted visual testing comprising the steps of:
    generating, under the direction of an associated processor unit, image data representative of a series of visual stimuli, inclusive of graphical images, text, and moving images;
    communicating the image data to a patient color video display unit;
    displaying, on the patient color video display unit, images corresponding to the image data;
    selectively generating a digital, binocular control signal as data representative of a multiplexing of left and right images;
    communicating the binocular control signal to a flickerless, binocular viewing system;
    acquiring patient feedback data from a patient after a display of each of a plurality of images generated on the patient color video display unit and the flickerless binocular viewing system;
    selectively controlling the associated processor unit so as to generate the image data and the binocular control signal in accordance with a clinician data input received from a clinician;
    generating, under the direction of the associated processor unit, audio data representative of a series of audio stimuli based on preselected criteria;
    communicating the audio data to a patient audio transducer;
    generating, on the patient audio transducer, sounds corresponding to the audio data;
    receiving, into a microphone, audio input from at least one of the patient and the clinician;
    selectively communicating digitized audio input to the associated processor unit;
    selectively archiving the digitized audio input;

selectively controlling the associated processor unit in accordance with the digitized audio input;

selectively generating, in the associated processor unit, an environmental control signal; and communicating the environmental control signal to a control interface for controlling at least one of an external associated indicator and lighting.

9. The method of computer-assisted visual testing of claim 8 further comprising the steps of:

monitoring an environmental condition associated with a patient; and selectively modifying the environmental control signal in accordance with a monitored environmental condition.

10. The method of computer-assisted visual testing of claim 9 further comprising the step of selecting, in accordance with the patient feedback data, at least one of 1) a text interface on the patient color video display, and 2) audio data, representative of a particular language selected by the patient.

11. The method of computer-assisted visual testing of claim 10 wherein the step of selectively controlling the associated processor unit in accordance with the clinician data input received from a clinician includes the step of controlling generation of images on the patient color video display unit and the binocular viewing system inclusive of stimuli data representative of at least one of a controlled size, optotype, image quantity, speed, animation, orientation, isolation, frequency, duration, position, contrast, brightness, color, fog/blur, binocular, stereoscopic pair, and specialized individual images for each eye.

12. A system for computer-assisted visual testing comprising:

at least one examination station, each examination station including:

a processor unit for generating image data representative of a series of visual stimuli based on preselected criteria, inclusive of graphical images, text, and moving images;

means for communicating the image data to a patient color video display unit;

a video display unit for displaying images corresponding to the image data;

means for generating a digital, binocular control signal as data representative of a multiplexing of left and right images;

means for communicating the binocular control signal to a binocular viewing system;

data input means for acquiring patient feedback data from a patient after a display of each of a plurality of images generated on at least one of the video display unit and the binocular viewing system;

means for controlling the processor unit so as to generate the image data and the binocular control signal in accordance with a clinician data input received from a clinician;

means for generating, under the direction of the processor unit, audio data representative of a series of audio stimuli based upon preselected criteria;

means for communicating the audio data to a patient audio transducer;

means for generating, on the patient audio transducer, sounds corresponding to the audio data;

a microphone for receiving audio input from at least one of the patient and the clinician;

means for communicating digitized audio input to the processor unit;

archiving means for electively archiving the digitized audio input;

means for controlling the processor unit in accordance with the digitized audio input;

means for selectively generating, in the processor unit, an environmental control signal; and means for communicating the environmental control signal to a control interface to control at least one of an external associated indicator and lighting.

13. The system according to claim 1, wherein said system includes a plurality of examination stations linked to each other via a communication network to allow data communication therebetween.

14. The system according to claim 12, wherein said system includes a plurality of examination stations linked to each other via a communication network to allow data communication therebetween.

15. A computerized vision patient examination and medical office management system comprising:

(A) at least one examination station, each examination station including:

(i) a processor system including, a central processor unit, random access memory disposed in the address space of the central processor unit for holding instructions and data, an input/output unit adapted to send and receive digital signals to and from the central processor unit, a display generator for selectively generating visual stimuli images based on preselected criteria, and a stereo signal controller selectively outputting a digital, binocular control signal;

(ii) a clinician unit in data communication with the processor system including, a first color video display unit adapted to display digital images based on preselected criteria, set by the processor system, a first data input unit adapted to receive practitioner input, and means for controlling the processor system in accordance with data received into the first data input unit;

(iii) a patient unit in data communication with the processor system including, a second color video display unit adapted to display digital images, including visual stimuli images, set by the processor system which is adapted to accommodate a scan rate of over 120 Hertz, a graphical generator for generating graphical images on the second color video display unit, a second data input unit adapted to receive patient data, means for communicating data representative of patient input to the processor system, and stereo signal output means adapted for selectively outputting the digital, binocular control signal received from the processor system to an associated binocular flickerless viewing system; and (iv) an audio output unit adapted to output digital audio sounds set by the processor system;

(B) at least one office management station for carrying out office management functions, including:

a processor system for processing and storing data, input means for inputting data, and output means for outputting data; and (C) a communication network for linking the at least one examination station and the at least one office management station for data communication therebetween.

16. The system of claim 15 further comprising a patient information database unit connected to the communication network, wherein said patient information database unit is accessible by the at least one examination station and the at least one office management station via the communication network.

17. A method of computer-assisted visual testing comprising the steps of:
- receiving data from an associated office management station via a communication network;
- generating in accordance with the received data, under the direction of an associated processor unit, image data representative of a series of visual stimuli, inclusive of graphical images, text, and moving images;
- communicating the image data to a patient color video display unit;
- displaying, on the patient color video display unit, images corresponding to the image data;
- selectively generating a digital, binocular control signal as data representative of a multiplexing of left and right images;
- communicating the binocular control signal to a flickerless, binocular viewing system;
- acquiring patient feedback data from a patient after a display of each of a plurality of images generated on at least one of the patient color video display unit and the flickerless binocular viewing system;
- selectively controlling the associated processor unit so as to generate the image data and the binocular control signal in accordance with a clinician data input received from a clinician;
- generating, under the direction of the associated processor unit, audio data representative of a series of audio stimuli based on preselected criteria;
- communicating the audio data to a patient audio transducer;
- generating, on the patient audio transducer, sounds corresponding to the audio data;
- receiving, into a microphone, audio input from at least one of the patient and the clinician;
- selectively communicating digitized audio input to the associated processor unit;
- selectively archiving the digitized audio input;
- selectively controlling the associated processor unit in accordance with the digitized audio input;
- selectively generating, in the associated processor unit, an environmental control signal; and
- communicating the environmental control signal to a control interface for controlling at least one of an external associated indicator and lighting.

18. A system for computer-assisted visual testing comprising:
(A) at least one examination station, each examination station including:
- a processor unit for generating image data representative of a series of visual stimuli based on preselected criteria, inclusive of graphical images, text, and moving images;
- means for communicating the image data to a patient color video display unit;
- a video display unit for displaying images corresponding to the image data;
- means for generating a digital, binocular control signal as data representative of a multiplexing of left and right images;
- means for communicating the binocular control signal to a binocular viewing system;
- data input means for acquiring patient feedback data from a patient after a display of each of a plurality of images generated on at least one of the video display unit and the binocular viewing system; and
- means for controlling the associated processor unit so as to generate the image data and the binocular control signal in accordance with a clinician data input received from a clinician;

(B) at least one office management station for carrying out office management functions, including:
- a processor system for processing and storing data,
- input means for inputting data, and
- output means for outputting data; and (C) a communication network for linking the at least one examination station and the at least one office management station for data communication therebetween.

19. The system for computer-assisted visual testing of claim 18 further comprising:
- means for selectively generating, in the processor system, an environmental control signal; and
- means for communicating the environmental control signal via the communication network to a controller interface to control at least one of an external associated indicator and lighting.

* * * * *